(12) United States Patent
Freeman et al.

(10) Patent No.: US 11,272,889 B2
(45) Date of Patent: Mar. 15, 2022

(54) EVALUATION OF RESPIRATORY VOLUME MONITORING (RVM) TO DETECT RESPIRATORY COMPROMISE IN ADVANCE OF PULSE OXIMETRY AND ELIMINATE FALSE DESATURATION ALARMS

(71) Applicant: Respiratory Motion, Inc., Waltham, MA (US)

(72) Inventors: Jenny E. Freeman, Weston, MA (US); Jordan Brayanov, Medford, MA (US); Daniel Eversole, Swampscott, MA (US); Malcolm G. Bock, Medfield, MA (US)

(73) Assignee: Respiratory Motion, Inc., Watertown, MA (US)

( * ) Notice: Subject to any disclaimer, the term of this patent is extended or adjusted under 35 U.S.C. 154(b) by 968 days.

(21) Appl. No.: 15/380,480

(22) Filed: Dec. 15, 2016

(65) Prior Publication Data

US 2017/0164909 A1 Jun. 15, 2017

Related U.S. Application Data

(60) Provisional application No. 62/416,400, filed on Nov. 2, 2016, provisional application No. 62/270,413, filed on Dec. 21, 2015, provisional application No. 62/267,787, filed on Dec. 15, 2015.

(51) Int. Cl.
| | | |
|---|---|---|
| *A61B 5/00* | (2006.01) |
| *A61B 5/08* | (2006.01) |
| *A61B 5/087* | (2006.01) |
| *A61B 5/145* | (2006.01) |

(52) U.S. Cl.
CPC .............. *A61B 5/742* (2013.01); *A61B 5/087* (2013.01); *A61B 5/0816* (2013.01); *A61B 5/14542* (2013.01); *A61B 5/7278* (2013.01); *A61B 5/746* (2013.01)

(58) Field of Classification Search
CPC ....... A61B 5/742; A61B 5/746; A61B 5/0816; A61B 5/14542; A61B 5/087; A61B 5/7278

See application file for complete search history.

(56) References Cited

U.S. PATENT DOCUMENTS

| | | | |
|---|---|---|---|
| 3,433,217 A | 3/1969 | Rieke et al. |
| 3,690,143 A | 9/1972 | Day et al. |
| 3,742,936 A | 7/1973 | Blanie et al. |

(Continued)

FOREIGN PATENT DOCUMENTS

| | | |
|---|---|---|
| AU | 2007201370 | 4/2007 |
| CN | 1034665 | 8/1989 |

(Continued)

OTHER PUBLICATIONS

PCT Search and Patentability Report for PCT/US2016/066930, dated Mar. 27, 2017.

(Continued)

*Primary Examiner* — Jacqueline Cheng
*Assistant Examiner* — Tho Q Tran
(74) *Attorney, Agent, or Firm* — Remenick PLLC

(57) ABSTRACT

Systems and methods of leveraging high-fidelity continuous respiratory volume monitoring for rapid patient assessment are disclosed herein.

24 Claims, 4 Drawing Sheets

(56) References Cited

U.S. PATENT DOCUMENTS

| | | | |
|---|---|---|---|
| 3,953,329 A * | 4/1976 | Updike | A61M 1/1698 210/638 |
| 4,036,217 A | 7/1977 | Ito et al. | |
| 5,058,583 A | 10/1991 | Geddes et al. | |
| 5,469,859 A | 11/1995 | Tsoglin et al. | |
| 5,735,284 A | 4/1998 | Tsoglin et al. | |
| 6,168,568 B1 | 1/2001 | Gavriely | |
| 6,173,198 B1 | 1/2001 | Schulze et al. | |
| 6,286,806 B1 | 9/2001 | Corcoran | |
| 6,366,803 B1 | 4/2002 | Fee | |
| 6,402,969 B1 | 6/2002 | Rodgers et al. | |
| 6,809,462 B2 | 10/2004 | Pelrine et al. | |
| 6,976,963 B2 | 12/2005 | Clift | |
| 7,196,317 B1 | 3/2007 | Meissner, II et al. | |
| 7,361,146 B1 | 4/2008 | Bharmi et al. | |
| 7,530,956 B2 | 5/2009 | Lewicke et al. | |
| 7,871,394 B2 | 1/2011 | Halbert et al. | |
| 8,096,962 B2 | 1/2012 | Palazzolo et al. | |
| 8,306,611 B2 | 11/2012 | Granov et al. | |
| 8,430,817 B1 * | 4/2013 | Al-Ali | A61B 5/742 600/301 |
| 9,615,743 B2 * | 4/2017 | Kruger | A61B 5/091 |
| 2002/0032383 A1 | 3/2002 | Weil et al. | |
| 2004/0039295 A1 * | 2/2004 | Olbrich | A61B 7/003 600/538 |
| 2004/0071337 A1 | 4/2004 | Jeung et al. | |
| 2004/0123667 A1 | 7/2004 | McGrath | |
| 2005/0033198 A1 | 2/2005 | Kehyayan et al. | |
| 2005/0042589 A1 * | 2/2005 | Hatlestad | A61B 5/0031 434/262 |
| 2005/0090753 A1 | 4/2005 | Goor et al. | |
| 2005/0107719 A1 | 5/2005 | Arad (Abbound) | |
| 2005/0113702 A1 | 5/2005 | Salla et al. | |
| 2006/0058600 A1 | 3/2006 | Eichler | |
| 2006/0241506 A1 | 10/2006 | Melker et al. | |
| 2006/0241513 A1 | 10/2006 | Hatlestad et al. | |
| 2007/0010764 A1 | 1/2007 | Palazzolo et al. | |
| 2007/0276300 A1 | 11/2007 | Olson et al. | |
| 2008/0312565 A1 | 12/2008 | Celik-Butler et al. | |
| 2009/0062672 A1 | 3/2009 | Sly et al. | |
| 2009/0149748 A1 | 6/2009 | Lenhardt et al. | |
| 2009/0227849 A1 | 9/2009 | Goor et al. | |
| 2009/0264789 A1 | 10/2009 | Molnar et al. | |
| 2009/0281838 A1 * | 11/2009 | Lynn | G06Q 50/24 705/3 |
| 2009/0326253 A1 | 12/2009 | Iding et al. | |
| 2009/0326353 A1 | 12/2009 | Watson et al. | |
| 2010/0049071 A1 | 2/2010 | Goor et al. | |
| 2010/0113904 A1 * | 5/2010 | Batchelder | A61B 5/14551 600/324 |
| 2010/0152600 A1 | 6/2010 | Droitcour et al. | |
| 2010/0228166 A1 | 9/2010 | Centen | |
| 2010/0241181 A1 | 9/2010 | Savage et al. | |
| 2010/0292544 A1 * | 11/2010 | Sherman | A61B 5/00 600/300 |
| 2011/0040713 A1 | 2/2011 | Colman et al. | |
| 2011/0077497 A1 | 3/2011 | Oster et al. | |
| 2011/0138323 A1 * | 6/2011 | Skidmore | A61M 16/0051 715/800 |
| 2011/0245712 A1 | 10/2011 | Patterson et al. | |
| 2011/0306850 A1 | 12/2011 | Hatlestad et al. | |
| 2012/0041279 A1 * | 2/2012 | Freeman | A61B 5/0205 600/301 |
| 2012/0165883 A1 | 6/2012 | Kalgren et al. | |
| 2013/0127621 A1 * | 5/2013 | Watson | G08B 21/02 340/573.1 |
| 2013/0187941 A1 | 7/2013 | Noon | |
| 2013/0276785 A1 | 10/2013 | Melker et al. | |
| 2013/0289366 A1 * | 10/2013 | Chua | A61B 5/02028 600/301 |
| 2013/0296823 A1 | 11/2013 | Melker et al. | |
| 2014/0073895 A1 | 3/2014 | Freeman et al. | |
| 2015/0031964 A1 * | 1/2015 | Bly | G16H 40/67 600/301 |
| 2015/0105632 A1 | 4/2015 | Melker et al. | |
| 2015/0120067 A1 * | 4/2015 | Wing | H02J 7/0013 700/282 |
| 2016/0120468 A1 * | 5/2016 | Mathew | A61B 5/01 600/301 |
| 2016/0350488 A1 * | 12/2016 | Stocker | G16H 50/20 |

FOREIGN PATENT DOCUMENTS

| | | |
|---|---|---|
| CN | 101496767 | 2/2009 |
| EP | 1302217 | 4/2003 |
| EP | 2008581 | 12/2008 |
| EP | 2018825 | 1/2009 |
| JP | 200070370 | 3/2000 |
| JP | 2007203041 | 8/2007 |
| JP | 2009240752 | 10/2009 |
| RU | 2250462 C1 * | 4/2005 |
| RU | 2454932 C1 * | 7/2012 |
| WO | WO0033733 | 6/2000 |
| WO | WO2006006871 | 7/2004 |
| WO | WO2007064682 | 6/2007 |
| WO | WO2007147505 | 12/2007 |
| WO | WO2008130549 | 10/2008 |
| WO | WO2009035965 | 3/2009 |
| WO | WO2009036312 | 3/2009 |
| WO | WO2010059049 | 5/2010 |

OTHER PUBLICATIONS

U.S. Appl. No. 12/677,216, Freeman et al.
U.S. Appl. No. 13/210,360, Freeman et al.
U.S. Appl. No. 13/554,346, Freeman et al.
U.S. Appl. No. 14/021,939, Freeman et al.
Zulkarneev R Kh. et al., A Hardware-Software System for Volumetric Calibration of Impedance Pneumograms, Biomedical Engineering, vol. 35, No. 1, 2001, pp. 48-51.
Pajic, et al, Model-driven safety analysis of closed-loop medical systems, IEEE Trans Industr Inform. vol. 10, pags. 1-35, p. 4, para. 1-2, Oct. 28, 2013.
European Search Report for EP 16876683, dated May 9, 2019.

\* cited by examiner

| | No Pt [%] | LMV in PACU | Recorded SpO$_2$ Alarms | | | | Opioids | | | |
|---|---|---|---|---|---|---|---|---|---|---|
| | | | Transient (1-min) | Hypoxemic events (≥2min) | | | No. Pt [%] | Dosage | Frequency | PACU LOS |
| | | [#/hr] | | False | True | RN Records | | [μg/kg/hr] | [Doses/hr] | [hr] |
| With Low MV: | 198 [76%] | 2.3 ±0.1 | 58 | 10 | 7 | 1 | 133 [67%] | 40 ±3 | 2.0 ±0.1 | 2.8 ±0.1 |
| No Low MV: | 61 [24%] | 0 | 29 | 9 | 0 | 1 | 33 [53%] | 33 ±4 | 2.3 ±0.2 | 2.4 ±0.1 |
| Total: | 259 [100%] | 1.8 ±0.1 | 87 | 19 | 7 | 2 | 166 [64%] | 39 ±2 | 2.1 ±0.1 | 2.7 ±0.1 |

EVALUATION OF RESPIRATORY VOLUME MONITORING (RVM) TO DETECT RESPIRATORY COMPROMISE IN ADVANCE OF PULSE OXIMETRY AND ELIMINATE FALSE DESATURATION ALARMS

REFERENCE TO RELATED APPLICATIONS

This application claims priority to U.S. Provisional Application No. 62/267,787 entitled "Continuous Respiratory Status Visualization Technique" filed Dec. 15, 2015, U.S. Provisional Application No. 62/270,413 entitled "Evaluation of Respiratory Volume Monitoring (RVM) to Detect Respiratory Compromise in Advance of Pulse Oximetry and Eliminate False Desaturation Alarms" filed Dec. 21, 2015, and U.S. Provisional Application No. 62/416,400 entitled "Respiratory Volume and $SpO_2$ Monitoring Devices and Methods" filed Nov. 2, 2016, the entirety of all of which are hereby incorporated by reference.

BACKGROUND

1. Field of the Invention

The invention is directed to systems and methods of visualization of continuous respiratory status. Specifically, the invention is directed to systems and methods of leveraging high-fidelity continuous respiratory volume monitoring for rapid patient assessment.

2. Background of the Invention

Surveillance of respiratory status is a critical component of patient care in any clinical setting. Unfortunately, current clinical practice relies on secondary indicators of respiratory status, usually oxygen saturation ($SpO_2$) measured by pulse oximetry, in lieu of monitoring ventilation. Early identification of respiratory insufficiency using real-time respiratory volume monitoring has the potential to allow clinicians to alter therapy in time to prevent more serious complications. A non-invasive monitor that rapidly and accurately measures ventilation metrics could help reduce the rate of false alarms generated by pulse oximetry. Ventilation metrics would have utility in virtually all patient care environments, from the battlefield or other sites of traumatic injury, through transport, throughout the hospital in both critical care and general ward locations, and post discharge into the patient's home.

Until recently, monitoring ventilation in non-intubated patients has been challenging. An FDA-approved non-invasive bio-impedance based respiratory volume monitor has become recently available that provides real-time digital respiratory data as well as continuous trends of minute ventilation (MV), tidal volume (TV) and respiratory rate (RR) in non-intubated patients. Previous clinical studies have demonstrated strong correlation (mean of 0.96, 95% CI from 0.93 to 0.99 for regular and erratic breathing) and clinically relevant accuracy (average error accuracy of 9.3% for MV, 9.0% for TV and 1.8% for RR) between the RVM and spirometric measurements. When compared with volume measurements collected from patients on a ventilator, either during mechanical ventilation or spontaneously breathing the RVM demonstrated an average MV and TV accuracy>90% and RR accuracy>95%. Additionally, RVM measurements were not substantially impacted by ineffective obstructed breaths associated with small volumes of air movement not exceeding anatomic dead space.

Inadequate ventilation is usually the precipitating event leading to respiratory depression or respiratory arrest if not detected and treated in time. Since capnography has not proven as useful in non-intubated patients as once hoped, clinicians generally rely on pulse oximetry, despite its well-documented limitations. This is especially challenging in clinical settings with supplemental oxygen delivery. In patients receiving supplemental oxygen, basing care on a selected threshold of $SpO_2$ considered concerning (which now ranges from <80% to <90% in various institutions) can be fatal by providing false assurance as to patient safety. Relying on saturation data can delay the diagnosis of significant under-ventilation, undetected hypercarbia, and impending respiratory failure.

Another well-documented problem associated with pulse oximetry is the high rate of false alarms, which has contributed to increasingly serious clinical concerns associated with alarm desensitization and fatigue. Clinicians, plagued by an excessive number of alarms, of which approximately 90% are false, have responded by disabling alarms, decreasing volume, changing settings, or ignoring alarms altogether. "Alarm safety" became a Joint Commission on Hospital Accreditation national patient safety goal in 2013, and in 2015 the Commission mandated that improvements be made to ensure that alarms on medical equipment are heard and responded to on time.

Epstein and colleagues at Vanderbilt found that $SpO_2$ alarms occur at a particularly high rate in the postanesthesia care unit (PACU). Their results indicate that 11.3%±0.02% of PACU patients experienced at least one hypoxemic episode ($SpO_2$ alarm sustained for >2 min). Timely resolution of hypoxemic events outside the operating room proved challenging, with 40.9%±0.02% of the hypoxemic events unresolved after 3 min. This was likely compounded by the fact that 68.8% of $SpO_2$ alarms occurred in the PACU more than 30 min after arrival, at a time associated with less ongoing attention and potentially less availability of advanced respiratory care providers. The authors suggested a reconsideration of staff allocation, which is not only costly, but may not necessarily improve patient safety. Rather, one could use an RVM for the early identification of respiratory compromise, not only providing a longer window for skilled anesthesia providers to arrive, but also alerting a clinician earlier to a patient's deteriorating condition. An additional advantage of this technology may come from its truncal electrode placement, which helps reduce sensor dislodgement and is not susceptible to extremity motion. This feature may allow the RVM to help clinicians identify $SpO_2$ alarms that are artifacts (i.e., false alarms) triggered by patient's motion or probe dislocation, in addition to revealing when potential hypoxemia is masked by the administration of supplemental oxygen.

The purpose of this study was to assess the ability of the RVM to detect respiratory depression in advance of a low $SpO_2$ measurement and to differentiate false from true $SpO_2$ alarms. We hypothesized that the RVM would detect respiratory depression significantly earlier than pulse oximetry and may help reduce the frequency of false alarms created by motion or other artifacts impacting $SpO_2$ measurements.

SUMMARY OF THE INVENTION

The present invention overcomes the problems and disadvantages associated with current strategies and designs and provides new tools and methods of visualizing respiratory status.

One embodiment of the invention is directed to a visualization technique, based on continuous respiratory volume monitoring (RVM) data, which allows clinicians to assess patient respiratory status quickly and efficiently. By reducing the variability of the high-fidelity RVM data while preserving key temporal and dimensional features, one is able to synthesize hours of patient data into simple and easy-to-interpret plots, allowing clinicians to make clinical decisions faster, with improved patient safety, reduced staff workload, and healthcare cost-savings.

One embodiment of the invention is directed to a method of displaying respiratory data of a patient. The method comprises the steps of obtaining respiratory data of a patient from at least one patient sensor, obtaining oxygen saturation ($SpO_2$) data of the patient, obtaining treatment data of the patient, outputting a visualization of the patient's respiratory status on a display device including the respiratory data, the $SpO_2$ data, and the treatment data, and triggering at least one of an audible or visual alarm upon a predetermined condition in the variability of the $SpO_2$ data being met.

In a preferred embodiment, the respiratory data includes at least one of minute ventilation (MV), tidal volume (TV), and respiratory rate (RR) of the patient. Preferably, the patient is non-intubated. In a preferred embodiment, the visualization of the patient's respiratory status comprises at least one indication of a treatment timeline of the patient, at least one indication of supplemental oxygen given to the patient, at least one indication of a low minute ventilation (LMV) event, at least one indication of a drug dose given to the patient, at least one indication of an apneic pause longer than a predefined duration; and at least one indication of a low $SpO_2$ events, wherein a LMV event occurs upon the MV of the patient falling below a predetermined MV of the patient for a predetermined period of time and a low $SpO_2$ event occurs upon the $SpO_2$ of the patient falling below a predefined $SpO_2$ percentage.

Preferably, the visualization of the patient's respiratory status includes a differentiation between true $SpO_2$ events and false $SpO_2$ events, wherein a true $SpO_2$ event occurs upon a low $SpO_2$ event occurring for a predefined period of time and a false $SpO_2$ event occurs upon a low $SpO_2$ event occurring for less than the predefined period of time. The alarm is preferably triggered only for true $SpO_2$ events. Preferably, the indication of a low minute ventilation (LMV) event includes the duration of the event and the severity of the event. In a preferred embodiment, the respiratory data are obtained continuously and the $SpO_2$ data are obtained upon at least one of the MV, TV, or RR of the patient at least one of meeting predefined criteria or exceeding a predefined range.

Preferably, the $SpO_2$ data are obtained continuously and the respiratory data is obtained upon at least one of the MV, TV, or RR of the patient at least one of meeting predefined criteria or exceeding a predefined range. In a preferred embodiment, the $SpO_2$ data are displayed upon predefined criteria being met. The $SpO_2$ data are preferably obtained or displayed if and only if MV measurements drop below, for example, 50%, 40%, or 30% of baseline MV. Preferably, $SpO_2$ data are obtained or displayed if and only if MV measurements drop below, for example, 50%, 40%, or 30% of predicted MV based on the patient's body surface area. Preferably, $SpO_2$ data are obtained or displayed if and only if MV measurements drop below, for example, 50%, 40%, or 30% of predicted MV based on the patient's ideal body weight.

In a preferred embodiment, $SpO_2$ data are obtained or displayed if and only if MV measurements exceeds, for example, 250%, 300%, or 350% of baseline MV. Preferably, $SpO_2$ data are obtained or displayed if and only if MV measurements exceeds, for example, 250%, 300%, or 350% of predicted MV based on the patient's body surface area. Preferably, $SpO_2$ data are obtained or displayed if and only if MV measurements exceeds, for example, 250%, 300%, or 350% of predicted MV based on the patient's ideal body weight. Preferably, $SpO_2$ measurements are obtained or displayed if and only a rate of change of MV measurements over time exceeds a predefined threshold.

In a preferred embodiment, upon both MV below a predefined range and $SpO_2$ below a predefined range the audible or visual alarm is triggered. Preferably, the respiratory data is collected from a ventilator, spirometer, pneumotachometer, or non-invasive respiratory volume monitoring device. Preferably, the method further comprises adjusting at least one respiratory setting on a ventilator in intubated patients or on a continuous positive airway pressure or a bilevel positive airway pressure machine in non-intubated patients.

Other embodiments and advantages of the invention are set forth in part in the description, which follows, and in part, may be obvious from this description, or may be learned from the practice of the invention.

In each group, the number of $SpO_2$ alarms recorded in the EHR was determined and PACU nurse records, the number of patients receiving opioids, the average dosage and frequency of opioid administration, and the PACU LOS.

DESCRIPTION OF THE INVENTION

As embodied and broadly described herein, the disclosures herein provide detailed embodiments of the invention. However, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention Continuous RVM data, $O_2$ supplementation status, $SpO_2$ alarm records and PCA opioid administration data is collected from each patient during their stay, for example, in the PACU following orthopedic surgery. Herein, as an example, a low MV event (LMVe) is defined as MV<40% $MV_{PRED}$ (based on the patient's BSA) sustained for at least 60 seconds. Low $SpO_2$ alarm limit can be, for example, set at <90% and sporadic low $SpO_2$ readings (<2 min) are preferably considered "false alarms."

Figure 3:
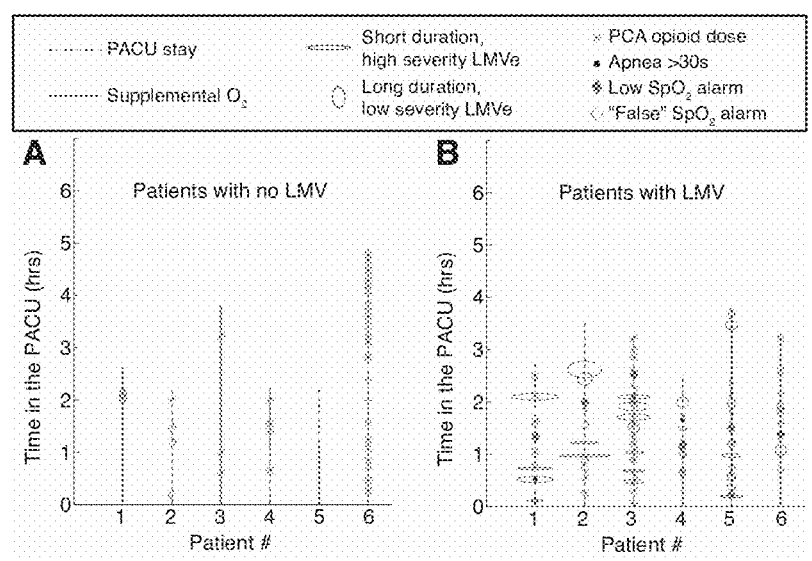
FIG. 3 Visualization of the Respiratory Status of Patients in the PACU. Each patient is visualized along an individual line, parallel to the Y-axis (see FIG. 1). The dashed blue line represents each patient's timeline in the PACU, with arrival at the PACU aligned with the X-axis. Supplemental $O_2$ is displayed as a solid red line overlaid on top of the dashed blue, spanning the regions where supplemental $O_2$ was delivered. Along each patient axis we display Low MV events with red ellipses. The length of each ellipse (along the y-axis) denotes the temporal duration of a Low MV event, whereas the width of each ellipse corresponds to the severity of each event with wider ellipses corresponding to more severe (i.e. lower MV) Low MV event. In addition, PCA opioid doses are visualized as green asterisks, apneic pauses longer than 30-sec as black dots, and Low $SpO_2$ alarms as purple diamonds. "False $SpO_2$ alarms" (i.e. 1-min Transient Alarms and False Desaturations) are displayed with hollow symbols and True Desaturations displayed with solid symbols.

Each patient is preferably visualized along an individual axis, parallel to the Y-axis. For example, as depicted in FIG. 3, the dashed line represents each patient's timeline in the PACU, with arrival at the PACU aligned with the X-axis. Supplemental $O_2$ is displayed as a solid line overlaid on top of the dashed line spanning the regions where supplemental $O_2$ was delivered. Along each patient axis the LMVe is displayed with ellipses. The length of each ellipse (along the y-axis) denotes the temporal duration of an LMVe or a cluster of LMVe (if in close succession), whereas the width of each ellipse corresponds to the severity of each event with wider ellipses corresponding to more severe (e.g. lower MV) LMVe. In addition, PCA opioid or other drug doses are visualized as asterisks, apneic pauses longer than 30-sec or another predefined duration as dots, and Low $SpO_2$ alarms as diamonds. "False $SpO_2$ alarms" are displayed with hollow symbols and true $SpO_2$ alarms lasting>2 min are displayed with solid symbols.

As more clinical decisions are driven by quantitative data, new ways of synthesizing and visualizing data can assist with interpretation and quicker patient assessment. This is particularly important when working with high-fidelity respiratory volume data in non-intubated patients. The naturally occurring variability in these data can make it challenging for a clinician to combine trends and correlative or causal effects from the raw metrics alone. For these reasons, a synthesized visualization may be able to assist not only with clinical decision making, but may also reduce workload and associated healthcare costs.

In one embodiment of the invention, the RVM monitor is continuously applied to the patient and the $SpO_2$ monitor is applied to the patient only when triggered by MV, TV, or RR measurements or a combination thereof that meet certain criteria or go outside of pre-defined range(s). In another embodiment, the $SpO_2$ monitor is also continuously applied to the patient, but measurements are obtained only when triggered by MV, TV, or RR measurements or a combination thereof that meet certain criteria or go outside of pre-defined range(s).

In another embodiment, the $SpO_2$ monitor is both applied and measurements from it are obtained continuously, however, internal algorithms determine when those measurements are displayed. In one embodiment, $SpO_2$ measurements are obtained and/or displayed if and only if MV measurements drop below 40% of baseline MV. In one embodiment, $SpO_2$ measurements are obtained and/or displayed if and only if MV measurements drop below 40% of predicted MV based on the patient's body surface area (BSA). In one embodiment, $SpO_2$ measurements are obtained and/or displayed if and only if MV measurements drop below 40% of predicted MV based on the patient's ideal body weight (IBW). In one embodiment, $SpO_2$ measurements are obtained and/or displayed if and only if MV measurements exceeds 300% of baseline MV. In one embodiment, $SpO_2$ measurements are obtained and/or displayed if and only if MV measurements exceeds 300% of predicted MV based on the patient's BSA. In one embodiment, $SpO_2$ measurements are obtained and/or displayed if and only if MV measurements exceeds 300% of predicted MV based on the patient's IBW. In one embodiment, $SpO_2$ measurements are obtained and/or displayed if and only the rate of change of MV measurements over time exceeds a pre-defined threshold (e.g. 1 L/min^2 or 20%/min).

In one embodiment, the MV is incorporated into standard early scoring systems instead of RR. In one embodiment, an algorithm based on a combination of one or more of MV, TV, or RR triggers the integration of $SpO_2$ measurements as above (e.g. one or more of continuously applied, intermittently applied, and continuously collected). In one embodiment, an algorithm based on a second-order features (e.g.

variance, kurtosis, entropy, and enthalpy) of one or more of MV, TV, or RR triggers the integration of $SpO_2$ measurements as above (e.g. one or more of continuously applied, intermittently applied, and continuously collected).

In one embodiment, MV, TV, RR measurements or second-order derived statistics of those measurement or a combination of these is used to filter $SpO_2$ measurements to exclude or minimize the impact of likely false measurement in data display, analysis, or clinical decision making algorithms. In one embodiment, a combination of Low MV outside pre-defined range and Low $SpO_2$ is preferably required to trigger an alert requiring clinical intervention or assessment. In another embodiment, the data from one of these combinations can be used for the diagnosis of respiratory depression, respiratory compromise, respiratory arrest, respiratory failure, need for intubation, need for re-intubation, need for extubation, transfer to higher acuity setting, transfer to lower acuity setting, discharge home, admission to hospital, need for treatment, monitoring the effectiveness of treatment or therapy, need and titration of $O_2$ administration, need or titration of CPAP or BiPAP or high flow $O_2$.

In one embodiment, MV, TV, or RR data may be collected from a ventilator, spirometer, pneumotachometer, or non-invasive RVM. Combined data can be used for adjustment of respiratory setting (e.g. PEEP or flow) on a ventilator in intubated patients or in continuous positive airway pressure or bilevel positive airway pressure (CPAP/BiPAP) machines in non-intubated patients. Algorithms based on the combined data as mentioned herein may use temporal lead/lag between measurements when integrating data together.

The following examples illustrate embodiments of the invention, but should not be viewed as limiting the scope of the invention.

EXAMPLES

A non-invasive, impedance-based respiratory volume monitor (RVM) was used to continuously and quantitatively measure real-time MV, TV, and RR. Thoracic PadSet electrodes were placed in the recommended positions (sternal notch, xiphoid, and right midaxillary line at the level of the xiphoid). Medical history, anthropometrics, and basic demographics were obtained. In this observational study, clinicians were blinded to the RVM measurements and perioperative patient care followed standard practice, i.e. no changes were made to pain management protocols, PACU care, or interventions based on RVM measurements.

RVM data collection was started preoperatively, continued during surgery (using either general or spinal anesthesia), and terminated upon discharge from the PACU. $SpO_2$ values, measured as part of the routine PACU care, were collected by the bedside monitor and oximetry system in clinical use. Time stamped $SpO_2$ values, routinely recorded at 60-second intervals, were obtained from the electronic health records (EHR). From the PACU nursing records, the following events, with approximate times noted, were obtained: PACU admission and discharge, supplemental oxygen (mode and flow rate), clinician-administered opioids (dose) and any clinician recorded desaturation events. Patients with post-operative pain were typically managed on patient-controlled analgesia (PCA) pumps using either hydromorphone 0.2 mg/ml or morphine 1 mg/ml. Dosing timestamps were obtained from the PCA log. The total opioid dose was calculated in Morphine Milligram Equivalents/kg (MME/kg) for each patient using the following conversion ratios: 1 mg morphine=1 MME; 0.13 mg hydromorphone=1 MME; 10 mcg fentanyl=1 MME.

Each patient's Predicted MV ($MV_{PRED}$), representing the expected MV during quiet respiration in the awake, non-intubated patient, was calculated based on BSA and patient gender. Measured MV ($MV_{MEASURED}$) was converted to Percent Predicted MV ($MV_{MEASURED}/MV_{PRED} \times 100\%$). Low MV was defined as MV less than 40% $MV_{PRED}$ sustained for a period of 1-min or longer. The criteria chosen for Low MV <40% $MV_{PRED}$ was originally based on the ARDSnet protocol for weaning patients off mechanical ventilation, which suggests that adequate ventilation associated with successful extubation is >40% of the predicted value for normal respiratory volumes and MV <40% $MV_{PRED}$ was subsequently used to define inadequate ventilation to risk-stratify patients in the PACU. Any measured Low MV within a 10-min period following the first Low MV alarm was considered part of the same event.

Correlating Minute Ventilation with Pulse Oximetry Data.

Timestamps for both RVM measurements (MV, TV, and RR) and $SpO_2$ values recorded in the EHR were aligned to facilitate the classification of pulse oximeter alarms. The pulse oximeter alarm (Low $SpO_2$) in the PACU was set at $SpO_2$<90% as per standard hospital protocol. In Table 1 patients were stratified based on the occurrence of Low MV. All terms and their abbreviations are summarized.

A Low $SpO_2$ recorded for 1-min was considered to be a "Transient Alarm," and Low $SpO_2$ sustained for period of 2-min or longer (i.e. a minimum of two consecutive one minute data points) was considered a "Hypoxemic Episode". Hypoxemic Episodes were stratified into "True Desaturation" if the Hypoxemic Episode was associated with a preceding Low MV and "False Desaturation" when the Hypoxemic Episode coincided with patient movement and/or pulse oximeter probe malposition. Both Transient Alarms and False Desaturations were considered to be "False Alarms". A True Desaturation was considered to be a "True Alarm".

Statistical Analysis.

Multi-factor analysis of variance (MFANOVA) was used to evaluate differences in patient demographics between different groups. Unpaired two-sided t-tests were used to compare length of stay (LOS) across groups and a Fisher's exact test was used to investigate the occurrence of Low MV with opioid administration and administration of supplemental oxygen. All analyses were performed in MATLAB R2012b, with a p<0.05 considered significant. All values in the manuscript are reported as mean±standard error of the mean (SEM), unless otherwise noted.

Data were obtained from 273 patients. Fourteen patients were excluded due to missing data ($SpO_2$, RVM) or withdrawal of consent. Of the remaining 259 patients (140 females, mean age, 67 years, range, 28-91 years; mean body mass index (BMI), 29.8 kg/m², range, 19.0-49.1 kg/m²) included in the analysis, 82 patients (32% of cohort) had general anesthesia and 177 (68%) had spinal anesthesia. Patients were monitored for an average of 2.7±0.1 hrs in the PACU.

Identification of True Desaturation by Monitoring Low MV.

The MV trends were aligned with recorded $SpO_2$ values to analyze: (1) the MV preceding and during a Low $SpO_2$ Alarm, to help differentiate True Desaturation and False Desaturation events and (2) severity and timing of a Low MV event related to a Low $SpO_2$ Alarm.

Figure 1:
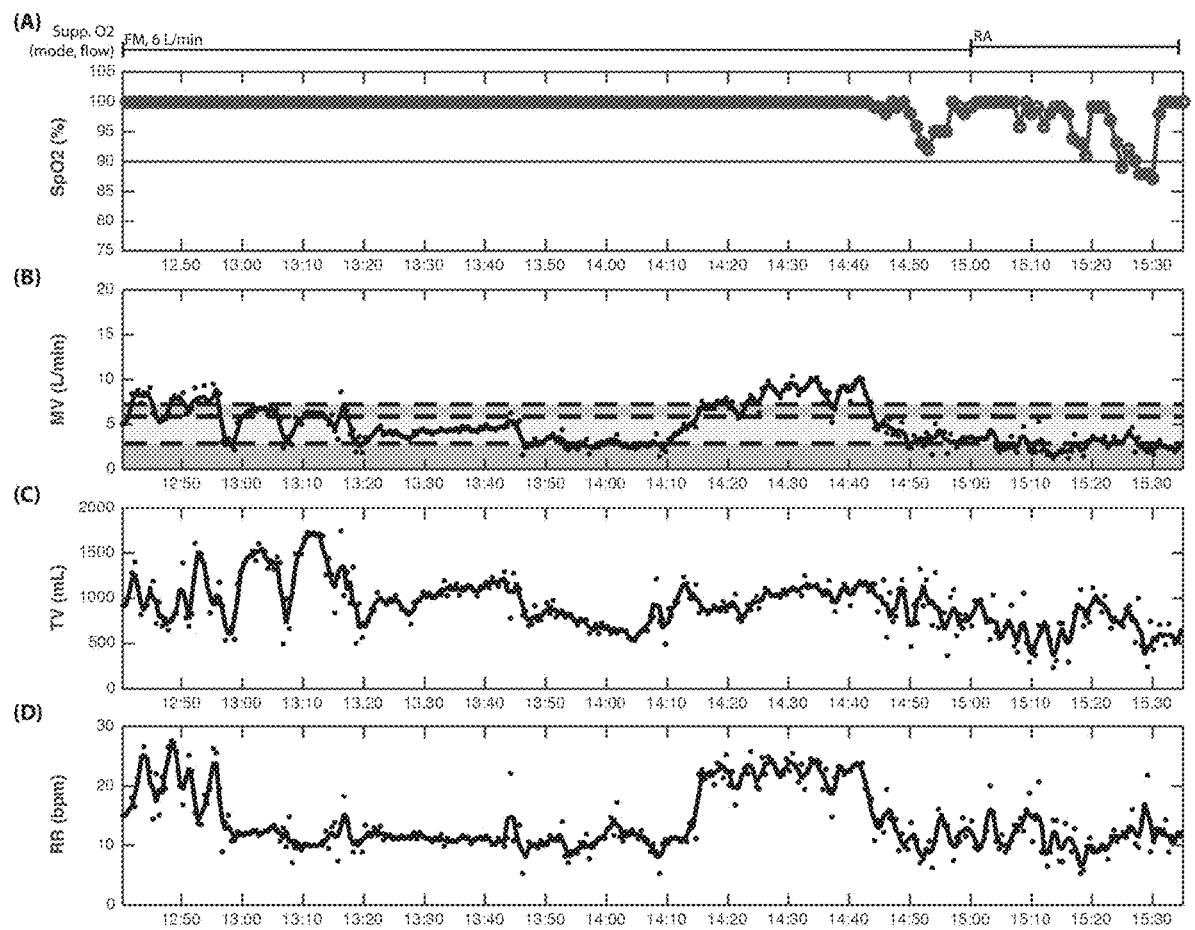
FIG. 1 A 70 y/o female patient (BMI: 36.7 kg/m$^2$, 7.2 L/min $MV_{PRED}$) with a 25-pack year smoking history and previous diagnosis of COPD, Type 2 Diabetes, and heart disease presented for right total hip replacement surgery. After surgery under general anesthesia, the patient was monitored in the PACU for 183-min with pulse oximetry and RVM. Here we present recorded $SpO_2$ values (A) aligned with the RVM trends of MV (B), TV (C), and RR (D). $SpO_2$ values (open blue circles) were recorded in the EHR at 1-min intervals. One-minute Transient Alarms and False Desaturation are indicated as red circles and True Desaturations filled red circles. In the PACU, the patient experienced a single 1-min Transient Alarm in addition to a single Hypoxemic Episode, lasting 3-min. The patient was initially placed on supplemental oxygen by facemask (6 L/min) and transitioned to room air during phase 3 of the PACU. A morphine PCA pump was implemented, but no doses were administered. The patient experienced 10 recurring Low MV events commencing 149-min prior to the True Desaturation with the most closely preceding Low MV event occurring 12.6-min prior to the True Desaturation. $SpO_2$ values remained steady, indicating the pulse oximeter was well seated on the patient's finger. Note that Low MV was more associated with a decrease in TV than RR.

FIG. 1 provides an example of a 70 y/o female patient, BMI: 36.7 kg/m², 7.2 L/min $MV_{PRED}$ who experienced a True Desaturation event. Over much of her 183-min PACU stay, the $MV_{MEASURED}$ was less than 80% $MV_{PRED}$, stabilizing at or below 40% $MV_{PRED}$ for the last 50-min of the PACU stay. It was during this period, readings from the pulse oximeter, which remained at 100% prior to this point, drifted to levels below 90%. The patient experienced 10 recurring Low MV events commencing 149-min prior to the True Desaturation with the most closely preceding Low MV event occurring 12.6-min prior to the True Desaturation.

Figure 2:
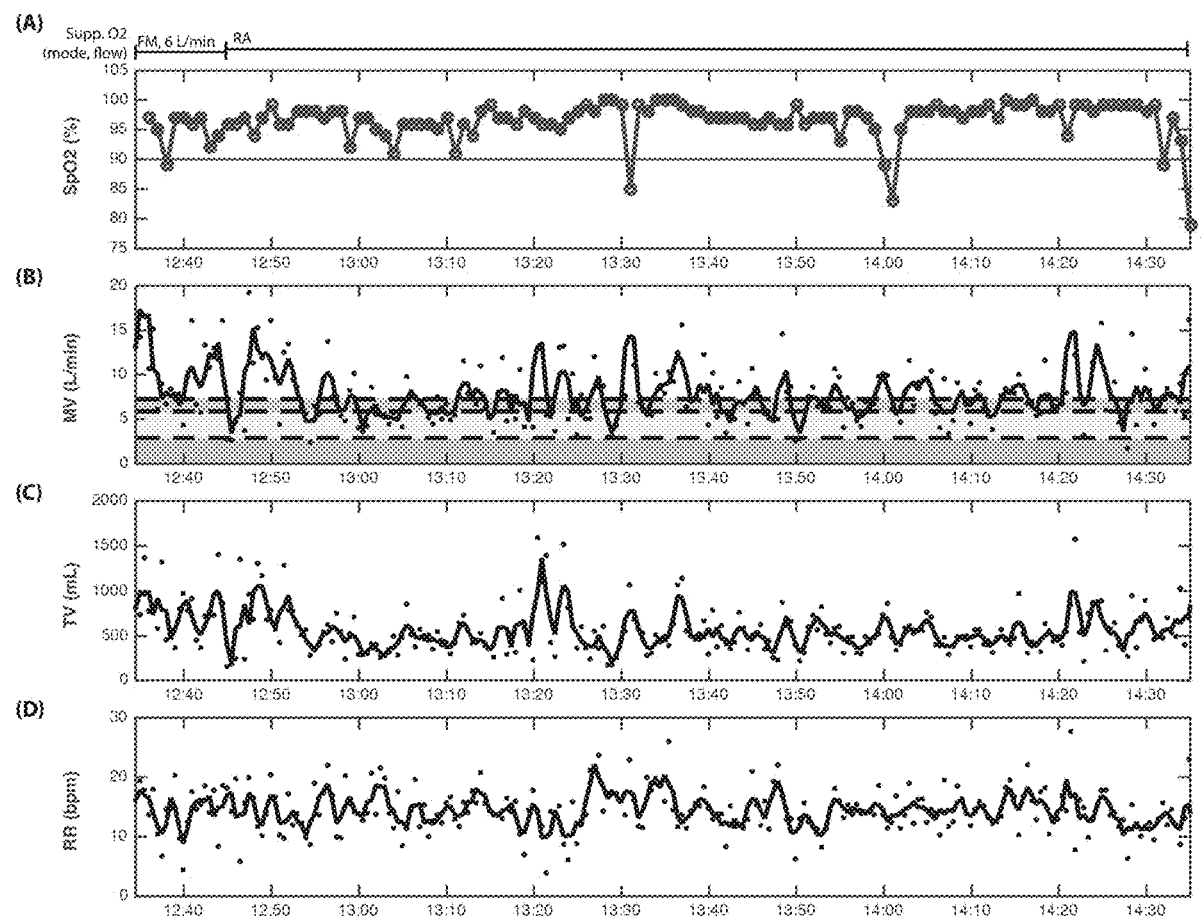
FIG. 2 Patient with Multiple False Alarms. A 63 y/o female patient (BMI: 29.1 kg/m$^2$, 7.0 L/min $MV_{PRED}$) with a 4.5-pack year smoking history and no diagnosed respiratory issues presented for right total knee arthroplasty/replacement. After surgery under spinal anesthesia, the patient was monitored in the PACU for 121-min with pulse oximetry and RVM. Here we present recorded $SpO_2$ values (A) aligned with the RVM trends of MV (B), TV (C), and RR (D). $SpO_2$ values (open blue circles) were recorded in the EHR at 1-min intervals. 1-min Transient Alarms and False Desaturation are indicated as red circles. In the PACU, the patient experienced four 1-min Transient Alarms in addition to a single Hypoxemic Episode, lasting 2-min. The patient was initially placed on supplemental oxygen by facemask (6 L/min) and within 15-min of PACU arrival transitioned to room air. A femoral nerve block for post-operative pain control was administered pre-op. As the block wore off, nursing records indicated pain scores>4 out of 10 and a hydromorphone PCA pump was implemented, from which 1-dose was administered. Admitted to the PACU with a $MV_{MEASURED}$ above 150% $MV_{PRED}$, the patient maintained a $MV_{MEASURED}$ centered about 100% $MV_{PRED}$ throughout her PACU stay. Concurrent with each Low $SpO_2$ alarm, the patient experienced large increases in MV. Contrasting with the $SpO_2$ signal reported in the True Desaturation patient, here $SpO_2$ values fluctuate continuously, considered to be from the pulse oximeter not being well seated on the patient's finger. Fluctuations in both MV and $SpO_2$ indicate excessive patient movement.

FIG. 2 provides an example of a 63 y/o female patient, BMI: 29.1 kg/m$^2$, 7.0 L/min $MV_{PRED}$ with multiple False Desaturation events. This patient was admitted to the PACU with a $MV_{MEASURED}$ above 150% $MV_{PRED}$. Over the course of her 121-min PACU stay, she experienced 4 Transient Alarms (1-min Low $SpO_2$) and 1 Hypoxemic Episode. Concurrent with all Low $SpO_2$ Alarms (both Hypoxemic Episodes and Transient Alarms), the patient experienced large increases in MV, coinciding with movement and/or exertion.

All Low $SpO_2$ Alarms were analyzed (i.e. Transient Alarms and Hypoxemic Episodes) recorded across the entire patient population to evaluate the relationship of Low MV to desaturation and to determine the number and proportion of True Desaturations (i.e. Hypoxemic Episodes preceded by Low MV events). Given multiple measurements and clinical interventions that occurred, a plot to facilitate visualization of key temporal and dimensional features was created. Low MV events and clinical markers (EHR recorded Low $SpO_2$ Alarm, supplemental $O_2$, and opioids) for each patient were temporally overlaid on a 1-dimensional axis representing each patient's PACU LOS, as shown in FIG. 3.

All 113 Low $SpO_2$ Alarms were concentrated in 46 of the 259 patients (18% of the cohort). Of the 113 Low $SpO_2$ Alarms, 87 (77%) were Transient Alarms (1-min Low $SpO_2$), and 26 (23%) met the criteria for a Hypoxemic Episode (i.e. >2 min). Of these Hypoxemic Episodes, 65% were 2-min, 27% were 3-min, 4% were 4-min, and 4%>5-min long. All recorded Hypoxemic Episodes were separated by at least 3 minutes and had no missing data. Hypoxemic Episodes occurred in 18 patients; 12 of these 18 patients had one or more accompanying Transient Alarm. Note that 74% of all Low $SpO_2$ Alarms occurred >30-min after admission to the PACU, which agrees with the 68.8% reported by Epstein et al (16).

$SpO_2$ is a Late Indicator of Respiratory Depression.

Correlation of Hypoxemic Episodes with RVM measurements shows that only 8 out of 113 (7%) Low $SpO_2$ Alarms were True Desaturations (identified in 7 patients—4 females; mean age, 69 years, range, 58-83 years; BMI, 27.2 kg/m$^2$, range, 21.9-36.7 kg/m$^2$; 6 of 7 received spinal anesthesia). True Desaturations were 2.5±0.3 min in length and the Low MV event most immediately preceding a True Desaturations occurred an average of 12.8±2.8 min earlier. Importantly, these True Desaturations generally followed repeated Low MV events. Patients with True Desaturation had on average 4.9±0.9 Low MV events commencing 71.4±16.5 min prior to a True Desaturation. Multi-factor ANOVA found no statistically significant difference in the demographics of the patients with True Desaturation (i.e. True Alarms) vs False Alarms (p>0.2 for height, weight, age, BMI, sex, and all cross-effects). The remaining 18 of 26 Hypoxemic Episodes coincided with excessive patient motion and adequate MV, i.e. MV>40% $MV_{PRED}$.

Stratification of Patients by Occurrence of Low MV

Of the 259 patients, 198 (76%) experienced at least one Low MV event (2.3±0.1 Low MV events per hour), with the remaining 61 (24%) patients maintaining adequate MV throughout their PACU stay. The LOS in the PACU for patients experiencing Low MV was significantly longer than those who maintained adequate MV (2.8±0.1 hr vs. 2.4±0.1 hr respectively (p<0.001)). Of the 259 patients, 202 (78%) were on supplemental oxygen for the majority of their PACU stay, and 137 (68%) of those 202 patients experienced at least one Low MV event without a Low $SpO_2$ Alarm recorded in the EHR. In contrast, of the remaining 57 (22%) patients who were maintained on room air during their PACU stay, 28 (49%) experienced at least one Low MV event without a Low $SpO_2$ Alarm recorded in the EHR (p<0.05).

Figure 4:
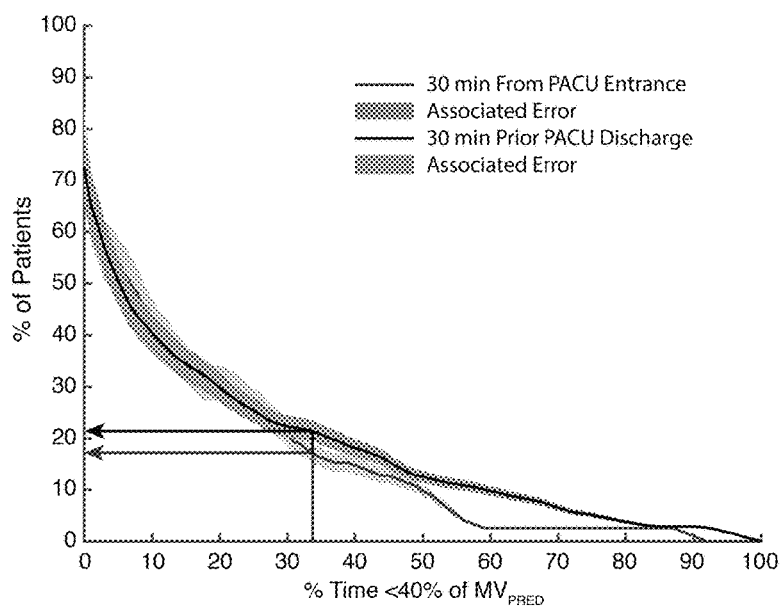
FIG. 4 Stratification of Patient Cohort by Occurrence of Low MV. The plot shows the percent of patients in which the RVM measured MV levels below the 40% $MV_{PRED}$ threshold. RVM data for the entire patient cohort was segmented into two important 30-min periods: the 30 minutes starting at PACU arrival and the 30 minutes prior to discharge from PACU.

The percent of time each patient maintained MV<40% $MV_{PRED}$ was further analyzed during the first and last 30-min in the PACU (FIG. 4). Arrows indicate the percentage of patients with MV below 40% of $MV_{PRED}$ for at least 10 minutes (one-third of each 30-min segment), indicating increased opioid sensitivity or other cause of respiratory depression and potentially a threat to patient safety. In the first 30-min in the PACU, approximately 18% of patients experienced Low MV for at least ⅓ of the time. This percentage remained at approximately 21% in the 30 minutes prior to discharge from the PACU, which could suggest that these patients may require RVM or other monitoring as they are transferred to the floor.

In 35 (18%) of the 198 patients with at least one Low MV event, there were 75 recorded Low $SpO_2$ Alarms in the EHR of which only one was noted in the PACU nursing records. Of the recorded 75 Low $SpO_2$ Alarms, 58 were 1-min Transient Alarms, 9 were False Desaturations, and 8 were True Desaturations.

In 11 (18%) of the 61 patients without a preceding Low MV event, there were 38-recorded Low $SpO_2$ Alarms in the EHR of which 29 were 1-min Transient Alarms and 9 were False Desaturations.

Opioids Increase Likelihood of Respiratory Depression; Low MV increases LOS

Patients were further stratified according to administration of opioids. 166 (64%) of 259 patients received opioids. Patients on opioids had an increased likelihood of Low MV (69% vs 80%, p<0.05). Furthermore, patients receiving opioids in the PACU had significantly longer LOS than those who did not receive opioids (2.9±0.1 hr vs. 2.3±0.1 hr, p<0.001). In the opioid group, the LOS in the PACU increased substantially with Low MV. The 133 (80%) of 166 patients on opioids with Low MV spent 75% longer in the PACU than the 33 (20%) patients on opioids without Low MV (3.0±0.1 hr vs. 1.7±0.2 hr, p<0.001).

Results show that the majority (93%) of $SpO_2$ alarms recorded in the EHR were likely false. Using the RVM, respiratory depression was detected in advance of all True Desaturations by 12.8±2.8 min from the immediately preceding Low MV event. In fact, if the healthcare providers caring for the patients studied here had been using the RVM for clinical assessment and treatment, they would have likely acted on the repeated Low MV alarms, which started an average of 71.4±16.5 min prior to each True Desaturation, possibly eliminating all of them. The lag between inadequate ventilation and the onset of hypoxemia as measured by the pulse oximeter is a critical period. Early signs of inadequate ventilation provided by the RVM could trigger assessment and treatment of the underlying cause before desaturation occurs, preventing rather than treating the hypoxemia.

A significantly larger fraction of the patients on supplemental $O_2$ had Low MV without a Low $SpO_2$ Alarm (68% vs 49%, p<0.05), indicating that supplemental oxygen likely masks the manifestation of respiratory depression as a desaturation. Data shows that supplemental oxygen increases the lag time before significant hypoxemia is detected below a preset $SpO_2$ threshold, potentially masking serious respiratory complications that can lead to respiratory failure and death. Results also show that pulse oximetry can detect periods of hypoventilation when a patient is breathing room air. Patients on oxygen should have additional monitoring of their ventilation status. While the data supports this view, it should not be overlooked that nearly half of the patients (49%) on room air also demonstrated periods of Low MV, indicating that pulse oximetry alone may also not be sufficient to monitor respiratory status of post-operative patients on room air who may have compromised ventilation from opioids or residual neuromuscular blockade.

Since pulse oximetry became universally implemented throughout the hospital, the issue of false alarms has increased in prevalence, leading to the Joint Commission's call for establishing policies and procedures for managing clinical alarms, most recently reinforced in their 2016 National Patient Safety Goals. Using continuous RVM in advance of or in conjunction with pulse oximetry has the potential to increase patient safety not only by providing earlier data as to deteriorating respiratory status, but also by reducing the number of false alarms. Developing protocols based on RVM data could mitigate the effects of alarm fatigue. Responding to all alarms drains clinical resources and time, in addition to not addressing the underlying problem. Additionally, RVM permits: (1) enhanced detection of increased opioid sensitivity, allowing for changes to opioid management based on each patient's individual response and helping to guide rational use of multimodal therapy and expensive non-opioids; (2) reduced PACU LOS; (3) improved triage of patients to an appropriate setting post-PACU, and (3) better determination of the most effective respiratory therapeutic strategy. Combined these features assist in increasing patient safety while reducing cost.

Length of stay in the PACU was significantly increased in patients with Low MV events (2.8±0.1 hr. vs 2.4±0.1 hr, $p<0.05$) and, as logic dictates. Opioid use increases the likelihood of a Low MV event in the PACU. However, data more dramatically show that patients receiving opioids who also experience Low MV events spent nearly 75% more time in the PACU vs patients receiving opioids who did not experience Low MV events (3.0±0.1 hr. vs. 1.7±0.2 hr., $p<0.001$). These findings indicate that instead of using a uniform opioid dosing regimen, clinicians could individualize opioid dosing or better select patients for expensive multimodal analgesic regimens based on real-time RVM data.

This study has several limitations. First, given the sample size, the current study did not stratify specific patient populations based on: (1) significant respiratory disease, e.g. chronic obstructive pulmonary disease, congestive heart failure; (2) obstructive sleep apnea; (3) decreased respiratory reserve, e.g. pregnant women, elderly, ultra-morbidly obese, children; (4) increased physiologic reserve, e.g. athletes (5) general versus spinal anesthesia. Second, events recorded in the EHR correlated poorly with PACU nursing records. The 1-min $SpO_2$ recordings represent snapshots rather than 1-min averages of $SpO_2$ values; combined with the 15-min resolution in the nursing records, the clinical indicators used to resolve hypoxemic events remain unclear. These limitations bring into question the reliability of nursing notes and EHR records as they currently are configured as the primary infrastructure to capture information as to patient respiratory status for retrospective analysis. When reviewing for quality issues, trying to reconstruct event timetables and actions taken can be very difficult, due to other clinical priorities leading to incomplete information records. Not uncommonly, the chart does not provide evidence or reasons for the patient needing to be urgently or emergently reintubated or having suffered a cardiopulmonary arrest.

Third, in this observational study, clinicians were blinded to the RVM measurements while pulse oximetry was used as part of routine care. As staff was unaware of Low MV and hence no clinical action steps were taken, the clinical condition of hypoventilation was not assessed or addressed. On this basis, the number of Low MV events per patient appears artificially inflated from what would be seen when the RVM technology is used to drive clinical assessment and action. Finally, the study was limited to the use of existing PACU monitoring technologies. Comparison of ventilation with $EtCO_2$ monitoring was not done because $EtCO_2$ monitoring was not implemented in the PACU in the study institution. Previous work has well documented accuracy of the RVM measurements in both intubated and non-intubated patients obviating the need to include spirometry. Additionally, adding spirometry complicates the study and enhance the Hawthorne effect.

Since measurement of MV using the RVM provides the earliest signal of respiratory insufficiency and, with truncal electrode placement, does not suffer from false alarms due to patient movement or probe dislodgement, there are several ways that the results presented here could be translated into clinical practice. One would be to monitor patient ventilation status continuously with RVM and obtain pulse oximetry readings only intermittently on a set schedule and also when the MV decreases below a given threshold. This approach is of particularly relevance to patient monitoring in a moving vehicle, where exogenous movement often renders oximetry monitoring suboptimal. Another is to create an algorithm that incorporated both continuous RVM and pulse oximetry data to define alarm parameters. Both of these methods provide a decrease in false alarms and improve patient safety.

The use of the basic RVM technology is not limited to brick-and-mortar hospital settings. Accurate, robust, and portable technologies for use in transport vehicles or mobile clinics, often found in disaster-struck regions or military conflict zones is important for the safety of patients where advanced respiratory care is not readily available. Continuous RVM monitoring of patients in these settings drive better management decisions regarding treatments and triaging that prevent otherwise serious consequences of severe respiratory compromise and minimize patient harm. Initial validation in the more controlled PACU setting is useful and carries extended value for other settings as well.

The RVM projects to be a clinical tool for identifying true respiratory depression and, when used in conjunction with $SpO_2$ monitoring, can reduce the number of false alarms, leading to less alarm fatigue and desensitization. Delivery of only meaningful alarms is particularly important in less intensely monitored and staffed clinical environments and would help hospitals meet The Joint Commission National Patient Safety Goal mandates to deal effectively with alarms. Using the RVM for monitoring non-intubated patients has great potential to improve patient safety, yield greater efficiency, and provide a method for respiratory assessment across the continuum of care.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims. Furthermore, the term "comprising of" includes the terms "consisting of" and "consisting essentially of."

TABLE 1

Definition of Terms and their Abbreviations

| Term | Abbreviation | Definition | Calculation |
|---|---|---|---|
| Measured Minute Volume | $MV_{MEASURED}$ | The real-time MV reported by the RVM | |
| Predicted Minute Volume | $MV_{PRED}$ | Expected MV under baseline conditions of quiet respiration in the awake, non-intubated patients | Male: BSA × 4<br>Female: BSA × 3.5 |
| Percent Predicted Minute Volume | % $MV_{PRED}$ | In percentage, the degree of deviation $MV_{MEASURED}$ is from the $MV_{PRED}$ | ($MV_{MEASURED}$/$MV_{PRED}$) × 100 |
| Adequate Minute Volume | Adequate MV | MV ≥40% $MV_{PRED}$ | |
| Low Minute Volume | Low MV | MV<40% $MV_{PRED}$ sustained for a period of 1-min or longer | |
| Low Minute Volume Event | Low MV event | Low MV within a 10-min period following the first Low MV alarm | |
| Pulse Oximeter Alarm | Low $SpO_2$ | $SpO_2$ <90% | |
| Transient Alarm | | $SpO_2$ <90% recorded for only 1-min | |
| Hypoxemic Episode | | $SpO_2$ <90% sustained for a period of 2-min or longer | |
| True Desaturation | | Low $SpO_2$ associated with a preceding Low MV event | |
| False Desaturation | | Low $SpO_2$ coinciding with Adequate MV and patient movement | |
| False Alarm | | Either a Transient Alarm or False Desaturation | |
| True Alarm | | A True Desaturation | |

The invention claimed is:

1. A method of displaying respiratory data of a patient comprising, on a processor:
   obtaining respiratory data of a patient from at least one patient sensor, wherein the respiratory data includes at least one of minute ventilation (MV), predicted MV, percent predicted MV, tidal volume (TV), and respiratory rate (RR) of the patient;
   obtaining oxygen saturation ($SpO_2$) data of the patient;
   obtaining treatment data of the patient;
   outputting a visualization of the patient's respiratory status on a display device including the respiratory data, the $SpO_2$ data, and the treatment data; and
   triggering at least one of an audible or visual alarm upon a predetermined condition in the variability of the $SpO_2$ data being met;
   wherein the visualization of the patient's respiratory status comprises at least one indication of a treatment timeline of the patient, at least one indication of supplemental oxygen given to the patient, at least one indication of a low minute ventilation (LMV) event, at least one indication of a drug dose given to the patient, at least one indication of an apneic pause longer than a predefined duration, at least one indication of a low $SpO_2$ events, wherein a LMV event occurs upon the MV of the patient falling below a predetermined MV of the patient for a predetermined period of time, or a low $SpO_2$ event occurs upon the $SpO_2$ of the patient falling below a predefined $SpO_2$ percentage; and
   wherein the visualization of the patient's respiratory status includes a differentiation between true $SpO_2$ events and false $SpO_2$ events, wherein a true $SpO_2$ event occurs upon a low $SpO_2$ event occurring for a predefined period of time and at least one of an abnormal MV, TV, or RR, and a false $SpO_2$ event occurs upon a low $SpO_2$ event occurring for less than the predefined period of time and at least one of an adequate MV, TV, or RR.

2. The method of claim 1, wherein the patient is non-intubated.

3. The method of claim 1, wherein the alarm is triggered only for true $SpO_2$ events.

4. The method of claim 1, wherein the indication of a low minute ventilation (LMV) event includes the duration of the event and the severity of the event.

5. The method of claim 1, wherein the respiratory data are obtained continuously and the $SpO_2$ data are obtained upon at least one of the MV, TV, or RR of the patient at least one of meeting predefined criteria or exceeding a predefined range.

6. The method of claim 1, wherein the $SpO_2$ data are obtained continuously and the respiratory data is obtained upon at least one of the MV, TV, or RR of the patient at least one of meeting predefined criteria or exceeding a predefined range.

7. The method of claim 1, wherein the $SpO_2$ data are displayed upon predefined MV, TV, or RR criteria being met.

8. The method of claim 1, wherein $SpO_2$ data are obtained or displayed if and only if MV measurements drop below 40% of baseline MV.

9. The method of claim 1, wherein SpO$_2$ data are obtained or displayed if and only if MV measurements drop below 40% of predicted MV based on the patient's body surface area.

10. The method of claim 1, wherein SpO$_2$ data are obtained or displayed if and only if MV measurements drop below 40% of predicted MV based on the patient's ideal body weight.

11. The method of claim 1, wherein SpO$_2$ data are obtained or displayed if and only if MV measurements exceeds 300% of baseline MV.

12. The method of claim 1, wherein SpO$_2$ data are obtained or displayed if and only if MV measurements exceeds 300% of predicted MV based on the patient's body surface area.

13. The method of claim 1, wherein SpO$_2$ data are obtained or displayed if and only if MV measurements exceeds 300% of predicted MV based on the patient's ideal body weight.

14. The method of claim 1, wherein SpO$_2$ measurements are obtained or displayed if and only a rate of change of MV measurements over time exceeds a predefined threshold.

15. The method of claim 1, wherein upon both MV below a predefined range and SpO$_2$ below a predefined range the audible or visual alarm is triggered.

16. The method of claim 1, wherein the respiratory data is collected from a ventilator, spirometer, pneumotachometer, or non-invasive respiratory volume monitoring device.

17. The method of claim 1, further comprising adjusting at least one respiratory setting on a ventilator in intubated patients or on a continuous positive airway pressure or a bilevel positive airway pressure machine in non-intubated patients.

18. A method of displaying respiratory data of a patient comprising, on a processor:
obtaining respiratory data of a patient from at least one patient sensor, wherein the respiratory data includes at least one of minute ventilation (MV), predicted MV, percent predicted MV, tidal volume (TV), and respiratory rate (RR) of the patient;
obtaining oxygen saturation (SpO$_2$) data of the patient;
obtaining treatment data of the patient;
outputting a visualization of the patient's respiratory status on a display device including the respiratory data, the SpO$_2$ data, and the treatment data; and
triggering at least one of an audible or visual alarm upon a predetermined condition in the variability of the SpO$_2$ data being met;
wherein SpO$_2$ data are obtained or displayed if and only if MV measurements drop below 40% of baseline MV.

19. A method of displaying respiratory data of a patient comprising, on a processor:
obtaining respiratory data of a patient from at least one patient sensor, wherein the respiratory data includes at least one of minute ventilation (MV), predicted MV, percent predicted MV, tidal volume (TV), and respiratory rate (RR) of the patient;
obtaining oxygen saturation (SpO$_2$) data of the patient;
obtaining treatment data of the patient;
outputting a visualization of the patient's respiratory status on a display device including the respiratory data, the SpO$_2$ data, and the treatment data; and
triggering at least one of an audible or visual alarm upon a predetermined condition in the variability of the SpO$_2$ data being met;
wherein SpO$_2$ data are obtained or displayed if and only if MV measurements drop below 40% of predicted MV based on the patient's body surface area.

20. A method of displaying respiratory data of a patient comprising, on a processor:
obtaining respiratory data of a patient from at least one patient sensor, wherein the respiratory data includes at least one of minute ventilation (MV), predicted MV, percent predicted MV, tidal volume (TV), and respiratory rate (RR) of the patient;
obtaining oxygen saturation (SpO$_2$) data of the patient;
obtaining treatment data of the patient;
outputting a visualization of the patient's respiratory status on a display device including the respiratory data, the SpO$_2$ data, and the treatment data; and
triggering at least one of an audible or visual alarm upon a predetermined condition in the variability of the SpO$_2$ data being met;
wherein SpO$_2$ data are obtained or displayed if and only if MV measurements drop below 40% of predicted MV based on the patient's ideal body weight.

21. A method of displaying respiratory data of a patient comprising, on a processor:
obtaining respiratory data of a patient from at least one patient sensor, wherein the respiratory data includes at least one of minute ventilation (MV), predicted MV, percent predicted MV, tidal volume (TV), and respiratory rate (RR) of the patient;
obtaining oxygen saturation (SpO$_2$) data of the patient;
obtaining treatment data of the patient;
outputting a visualization of the patient's respiratory status on a display device including the respiratory data, the SpO$_2$ data, and the treatment data; and
triggering at least one of an audible or visual alarm upon a predetermined condition in the variability of the SpO$_2$ data being met;
wherein SpO$_2$ data are obtained or displayed if and only if MV measurements exceeds 300% of baseline MV.

22. A method of displaying respiratory data of a patient comprising, on a processor:
obtaining respiratory data of a patient from at least one patient sensor, wherein the respiratory data includes at least one of minute ventilation (MV), predicted MV, percent predicted MV, tidal volume (TV), and respiratory rate (RR) of the patient;
obtaining oxygen saturation (SpO$_2$) data of the patient;
obtaining treatment data of the patient;
outputting a visualization of the patient's respiratory status on a display device including the respiratory data, the SpO$_2$ data, and the treatment data; and
triggering at least one of an audible or visual alarm upon a predetermined condition in the variability of the SpO$_2$ data being met;
wherein SpO$_2$ data are obtained or displayed if and only if MV measurements exceeds 300% of predicted MV based on the patient's body surface area.

23. A method of displaying respiratory data of a patient comprising, on a processor:
obtaining respiratory data of a patient from at least one patient sensor, wherein the respiratory data includes at least one of minute ventilation (MV), predicted MV, percent predicted MV, tidal volume (TV), and respiratory rate (RR) of the patient;
obtaining oxygen saturation (SpO$_2$) data of the patient;
obtaining treatment data of the patient;

outputting a visualization of the patient's respiratory status on a display device including the respiratory data, the $SpO_2$ data, and the treatment data; and triggering at least one of an audible or visual alarm upon a predetermined condition in the variability of the $SpO_2$ data being met;

wherein $SpO_2$ data are obtained or displayed if and only if MV measurements exceeds 300% of predicted MV based on the patient's ideal body weight.

24. A method of displaying respiratory data of a patient comprising, on a processor:

obtaining respiratory data of a patient from at least one patient sensor, wherein the respiratory data includes at least one of minute ventilation (MV), predicted MV, percent predicted MV, tidal volume (TV), and respiratory rate (RR) of the patient;

obtaining oxygen saturation ($SpO_2$) data of the patient;

obtaining treatment data of the patient;

outputting a visualization of the patient's respiratory status on a display device including the respiratory data, the $SpO_2$ data, and the treatment data; and triggering at least one of an audible or visual alarm upon a predetermined condition in the variability of the $SpO_2$ data being met;

wherein $SpO_2$ measurements are obtained or displayed if and only a rate of change of MV measurements over time exceeds a predefined threshold.

* * * * *